(12) United States Patent
Takahashi

(10) Patent No.: US 12,307,662 B2
(45) Date of Patent: May 20, 2025

(54) INFORMATION PROCESSING SYSTEM, INFORMATION PROCESSING METHOD, AND INFORMATION PROCESSING PROGRAM

(71) Applicant: FUJIFILM Corporation, Tokyo (JP)

(72) Inventor: Azuma Takahashi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 487 days.

(21) Appl. No.: 17/746,973

(22) Filed: May 18, 2022

(65) Prior Publication Data

US 2022/0277448 A1 Sep. 1, 2022

Related U.S. Application Data

(63) Continuation of application No. PCT/JP2020/039372, filed on Oct. 20, 2020.

(30) Foreign Application Priority Data

Dec. 10, 2019 (JP) ................................. 2019-223152

(51) Int. Cl.
*G06K 9/00* (2022.01)
*A61K 35/12* (2015.01)
(Continued)

(52) U.S. Cl.
CPC ........... *G06T 7/0012* (2013.01); *G16H 30/20* (2018.01); *G06T 2207/30096* (2013.01)

(58) Field of Classification Search
CPC ....... G06K 9/00; A61B 8/565; G06F 16/2477; A61K 35/12; G06T 7/00
(Continued)

(56) References Cited

U.S. PATENT DOCUMENTS 8,036,434 B2 10/2011 Hewett et al.
8,218,835 B2 * 7/2012 Matsuda ................ A61B 5/055
382/160
(Continued)

FOREIGN PATENT DOCUMENTS

JP 2001256498 9/2001
JP 2003116838 4/2003
(Continued)

OTHER PUBLICATIONS

"International Search Report (Form PCT/ISA/210) of PCT/JP2020/039372," mailed on Dec. 28, 2020, with English translation thereof, pp. 1-6.
(Continued)

*Primary Examiner* — Seyed H Azarian
(74) *Attorney, Agent, or Firm* — JCIPRNET

(57) ABSTRACT

An information processing system, an information processing method, and a non-transitory computer readable recording medium storing an information processing program that optimize a second process that is performed for a medical image after a first process are provided. An information processing system includes an automatic processing server that includes a CPU-20 and a storage unit storing instructions executable by the CPU-20, and a workstation that includes a CPU-30 and a storage unit storing instructions executable by the CPU-30. The CPU-20 carries out an image analysis for a medical image as a first process. The CPU-30 specifies a second process that depends on a processing result of the first process, from among a plurality of processes performable by a plurality of applications, and performs the second process for the medical image subjected to the first process.

9 Claims, 9 Drawing Sheets

(51) Int. Cl.
　　　*G06T 7/00*　　　(2017.01)
　　　*G16H 30/20*　　(2018.01)
(58) Field of Classification Search
　　　USPC ....... 382/100, 103, 128–134, 154, 156, 160,
　　　　　　　　382/162, 168, 173, 181, 206, 214, 224,
　　　　　　　　382/232, 254, 274, 276, 286–291, 305,
　　　　　　　　　　　　　382/312, 218–219; 378/4, 21;
　　　　　　　　　　　　　　　　　　　　　707/999.107
　　　See application file for complete search history.

(56) References Cited

U.S. PATENT DOCUMENTS

| | | | | |
|---|---|---|---|---|
| 8,682,049 | B2* | 3/2014 | Zhao | G06Q 10/103 |
| | | | | 382/128 |
| 9,075,851 | B2* | 7/2015 | Kilian | G06F 16/2477 |
| 9,964,617 | B2 | 5/2018 | Sueoka et al. | |
| 2005/0125411 | A1* | 6/2005 | Kilian | G06F 16/2477 |
| 2007/0269001 | A1 | 11/2007 | Maschke | |
| 2008/0059244 | A1* | 3/2008 | Fujita | G16H 30/20 |
| | | | | 707/999.107 |
| 2017/0032089 | A1* | 2/2017 | Kanada | G16H 30/20 |
| 2018/0137244 | A1* | 5/2018 | Sorenson | A61B 8/565 |

FOREIGN PATENT DOCUMENTS

| | | |
|---|---|---|
| JP | 2006326314 | 12/2006 |
| JP | 2007181482 | 7/2007 |
| JP | 2012232111 | 11/2012 |
| WO | 2009104459 | 8/2009 |

OTHER PUBLICATIONS

"International Preliminary Report on Patentability (Form PCT/IPEA/409) of PCT/JP2020/039372," completed on May 24, 2021, with English translation thereof, pp. 1-6.

* cited by examiner

FIG. 4

| AUTOMATIC PROCESSING SERVER | | WORKSTATION | | 42 |
|---|---|---|---|---|
| FIRST PROCESS | PROCESSING RESULT | SECOND PROCESS | PRIORITY RANK | |
| BONE FRACTURE CAD | BONE FRACTURE IS PRESENT | THREE-DIMENSIONAL IMAGE GENERATION | 1 | |
| | | SURFACE DISPLAY | 2 | |
| | | ...... | ...... | |
| | | RETENTION PERIOD: 6 MONTHS | | |
| TUMOR DETECTION CAD | MALIGNANT | METASTASIS ANALYSIS | 1 | |
| | | PAST IMAGE COMPARISON | 2 | |
| | | THREE-DIMENSIONAL IMAGE GENERATION | 3 | |
| | | ...... | ...... | |
| | | RETENTION PERIOD: 6 MONTHS | | |
| | BENIGN | METASTASIS ANALYSIS | 1 | |
| | | THREE-DIMENSIONAL IMAGE GENERATION | 2 | |
| | | ...... | ...... | |
| | | RETENTION PERIOD: 3 MONTHS | | |
| ...... | ...... | ...... | ...... | |

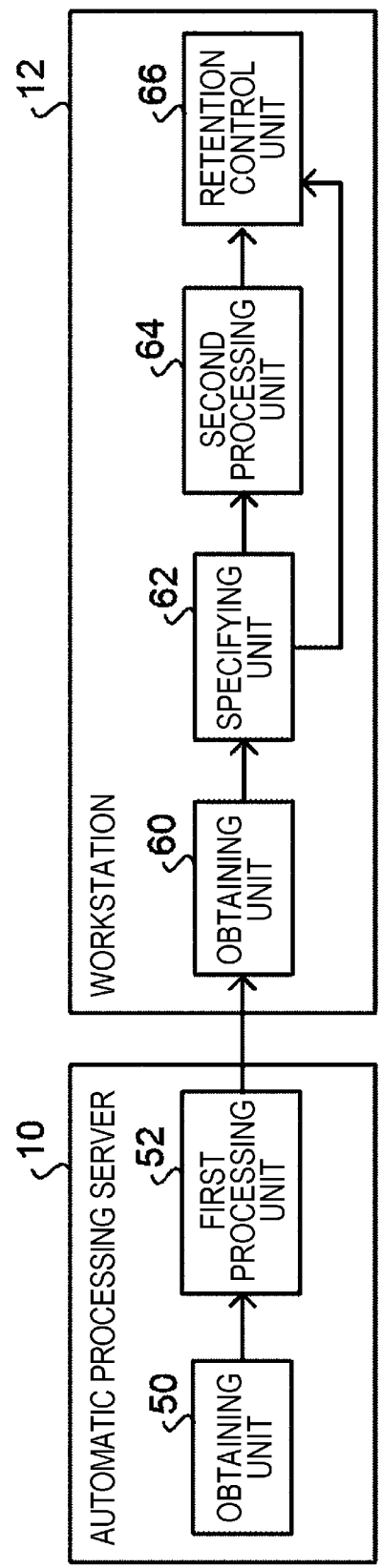

INFORMATION PROCESSING SYSTEM, INFORMATION PROCESSING METHOD, AND INFORMATION PROCESSING PROGRAM

CROSS-REFERENCE TO RELATED APPLICATIONS

This application is a Continuation of PCT International Application No. PCT/JP2020/039372 filed on Oct. 20, 2020, which claims priority under 35 U.S.C § 119(a) to Japanese Patent Application No. 2019-223152 filed on Dec. 10, 2019. Each of the above application(s) is hereby expressly incorporated by reference, in its entirety, into the present application.

BACKGROUND OF THE INVENTION

1. Field of the Invention

The present disclosure relates to an information processing system, an information processing method, and a non-transitory computer readable recording medium storing an information processing program.

2. Description of the Related Art

Techniques used in a case where a plurality of processes are automatically performed for a medical image, for optimizing, for example, the processing method are currently available. For example, JP2006-326314A discloses a technique in which for preprocessing performed for measurement data including image data and for post-processing performed after the preprocessing, a post-processing method for the post-processing that does not depend on the preprocessing is selected. In the technique disclosed in JP2006-326314A, the measurement data is parsed in connection with context data detected or derived in accordance with the format of the measurement data, and a post-processing method optimally designed for the measurement data is selected.

SUMMARY OF THE INVENTION

With techniques of the related art, each of the processes corresponding to measurement data is performed in preprocessing or post-processing; however, a process that is not necessary in actuality may be performed in post-processing, and it is not necessarily the case that optimization is satisfactorily attained. For example, with the technique disclosed in JP2006-326314A, for measurement data conforming to, for example, the DICOM (Digital Imaging and Communications in Medicine) standard, a process to be performed as post-processing is selected on the basis of the DICOM standard. In this case, a process that is not necessary in actuality may be selected as post-processing.

The present disclosure has been made in view of the above-described circumstances and provides an information processing system, an information processing method, and a non-transitory computer readable recording medium storing an information processing program that can optimize a second process that is performed for a medical image after a first process.

To achieve the object described above, an information processing system according to a first aspect of the present disclosure includes: at least one processor; and a memory configured to store an instruction and optimization information of a plurality of processes, executable by the processor, the processor being configured to carry out an image analysis for a medical image as a first process, specify, referring to the optimization information, a second process that depends on a processing result of the first process, from among the plurality of processes, and perform the optimized second process for the medical image subjected to the first process, in which the optimization information includes information indicating a correspondence between the processing result of the first process and at least one of the plurality of processes that are performed depending on the processing results of the first process, a retention period of the processing results of the plurality of processes or priority ranks of performing the plurality of processes.

An information processing system according to a second aspect of the present disclosure is the information processing system according to the first aspect, in which the processor is configured to specify a retention period of a processing result of the second process, the retention period depending on the processing result of the first process, and retain the processing result of the second process for the specified retention period.

An information processing system according to a third aspect of the present disclosure is the information processing system according to the first or second aspect, in which the processor is configured to specify, in a case where the second process includes two or more processes, priority ranks of the plurality of processes depending on the processing result of the first process, and perform the two or more processes included in the second process on the basis of the specified priority ranks.

An information processing system according to a fourth aspect of the present disclosure is the information processing system according to any one of the first to third aspects, in which the processor is configured to specify a process that is not to be performed as the second process from among the plurality of processes.

An information processing system according to a fifth aspect of the present disclosure is the information processing system according to any one of the first to fourth aspects, in which the first process includes a process of detecting presence or absence of a matter of concern from the medical image, and the processor is configured to not specify the second process in a case where the processing result of the first process includes a detection result indicating that the matter of concern is not present.

An information processing system according to a sixth aspect of the present disclosure is the information processing system according to any one of the first to fifth aspects, in which the medical image is a medical image conforming to a DICOM (Digital Imaging and Communications in Medicine) standard, and the plurality of processes are processes determined in accordance with a tag of the DICOM.

To achieve the object described above, an information processing system according to a seventh aspect of the present disclosure is an information processing system including: a first processing apparatus including at least one processor; and a second processing apparatus including at least one processor and a storage that stores optimization information of a plurality of processes executable by the processor, the processor of the first processing apparatus being configured to carry out an image analysis for a medical image as a first process, the processor of the second processing apparatus being configured to specify, referring to the optimization information, a second process that depends on a processing result of the first process, from among the plurality of processes, and perform the optimized second process for the medical image subjected to the first process, in which the optimization information includes information indicating a correspondence between the processing result of the first process and at least one of the plurality of processes that are performed depending on the processing results of the first process, a retention period of the processing results of the plurality of processes or priority ranks of performing the plurality of processes.

To achieve the object described above, an information processing method according to an eighth aspect of the present disclosure is an information processing method in which a computer performs a process including: carrying out an image analysis for a medical image as a first process, specifying, referring to optimization information of a plurality of processes, a second process that depends on a processing result of the first process, from among the plurality of processes, and performing the optimized second process for the medical image subjected to the first process, in which the optimization information includes information indicating a correspondence between the processing result of the first process and at least one of the plurality of processes that are performed depending on the processing results of the first process, a retention period of the processing results of the plurality of processes or priority ranks of performing the plurality of processes.

To achieve the object described above, a non-transitory computer readable recording medium storing an information processing program according to a ninth aspect of the present disclosure is an information processing program for causing a computer to perform a process including: carrying out an image analysis for a medical image as a first process, specifying, referring to the optimization information of a plurality of processes, a second process that depends on a processing result of the first process, from among the plurality of processes, and performing the second process for the medical image subjected to the first process, in which the optimization information includes information indicating a correspondence between the processing result of the first process and at least one of the plurality of processes that are performed depending on the processing results of the first process, a retention period of the processing results of the plurality of processes or priority ranks of performing the plurality of processes.

According to the present disclosure, it is possible to optimize a second process that is performed for a medical image after a first process.

BRIEF DESCRIPTION OF THE DRAWINGS

FIG. 4 is a diagram illustrating an example of optimization information;

FIG. 5 is a block diagram illustrating an example functional configuration of the automatic processing server and that of the workstation;

DESCRIPTION OF THE PREFERRED EMBODIMENTS

Hereinafter, an embodiment of the technique of the present disclosure will be described in detail with reference to the drawings.

Figure 1:
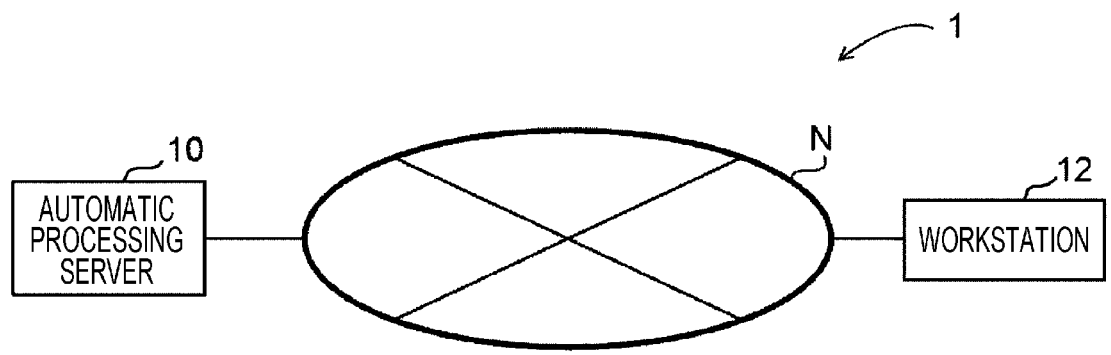
FIG. 1 is a block diagram illustrating an example configuration of an information processing system.

First, an information processing system 1 of the present embodiment will be described with reference to FIG. 1. FIG. 1 is a block diagram illustrating an example configuration of the information processing system 1 of the present embodiment. As illustrated in FIG. 1, the information processing system 1 of the present embodiment includes an automatic processing server 10 and a workstation 12. The automatic processing server 10 and the workstation 12 are connected to a network N and are capable of communicating with each other over the network N. Although FIG. 1 illustrates a form in which the information processing system 1 includes one automatic processing server 10 and one workstation 12, there is no limitation on the number of automatic processing servers 10 and the number of workstations 12 included in the information processing system 1.

The automatic processing server 10 is, for example, a cloud server configured in a cloud and performs a first process, which will be described in detail below. The automatic processing server 10 of the present embodiment is an example of a first processing apparatus in the present disclosure. Note that the first processing apparatus in the present disclosure is not limited to a cloud server, which is, for example, the automatic processing server 10 of the present embodiment, and may be, for example, a workstation or a personal computer. The workstation 12 is, for example, a computer that is installed in a hospital where examinations of subjects are conducted, and performs a second process, which will be described in detail below. The workstation 12 of the present embodiment is an example of a second processing apparatus in the present disclosure. Note that the second processing apparatus in the present disclosure is not limited to a workstation, which is, for example, the workstation 12 of the present embodiment, and may be, for example, a personal computer or a tablet computer. Each of the automatic processing server 10 and the workstation 12 may be constituted by a plurality of apparatuses.

Figure 2:
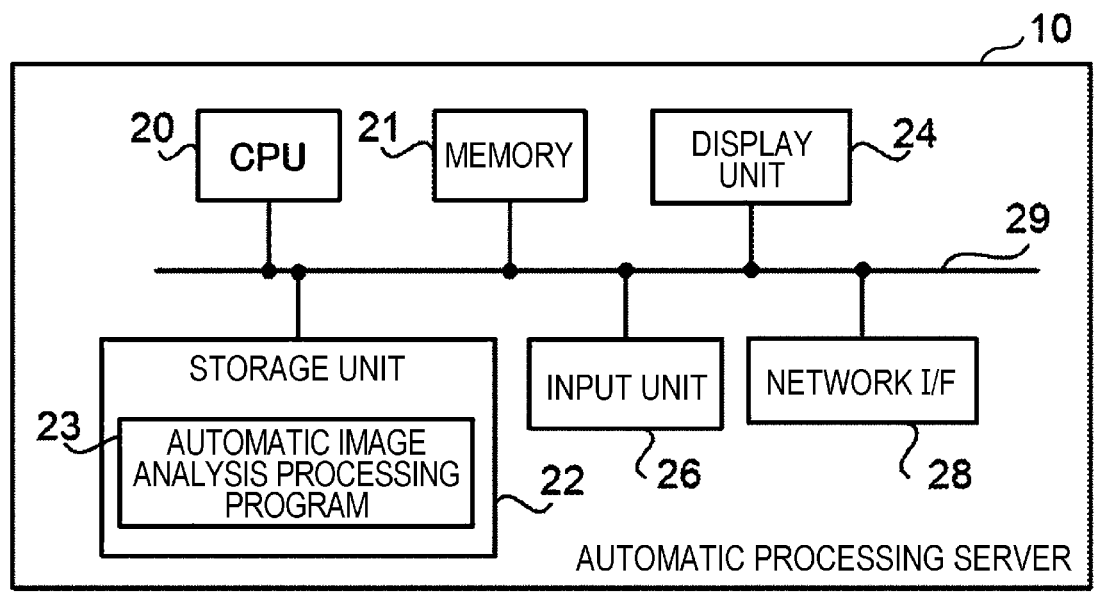
FIG. 2 is a block diagram illustrating an example hardware configuration of an automatic processing server.

Next, an example hardware configuration of the automatic processing server 10 of the present embodiment will be described with reference to FIG. 2. As illustrated in FIG. 2, the automatic processing server 10 includes a CPU (central processing unit) 20, a memory 21, which is a temporary memory area, and a storage unit 22, which is a nonvolatile memory.

The automatic processing server 10 includes a display unit 24, which is, for example, a liquid crystal display, an input unit 26, which is, for example, a keyboard or a mouse, and a network I/F (interface) 28, which is connected to the network N. Note that the display unit 24 and the input unit 26 may be integrated into a touch panel display. The CPU 20, the memory 21, the storage unit 22, the display unit 24, the input unit 26, and the network I/F 28 are connected to a bus 29 so as to be able to communicate with each other.

The storage unit 22 is implemented as, for example, an HDD (hard disk drive), an SSD (solid state drive), or a flash memory. In the storage unit 22 that is a storage medium, an automatic image analysis processing program 23 is stored. The CPU 20 reads from the storage unit 22 and loads to the memory 21 the automatic image analysis processing program 23 and executes the loaded automatic image analysis processing program 23.

Figure 3:
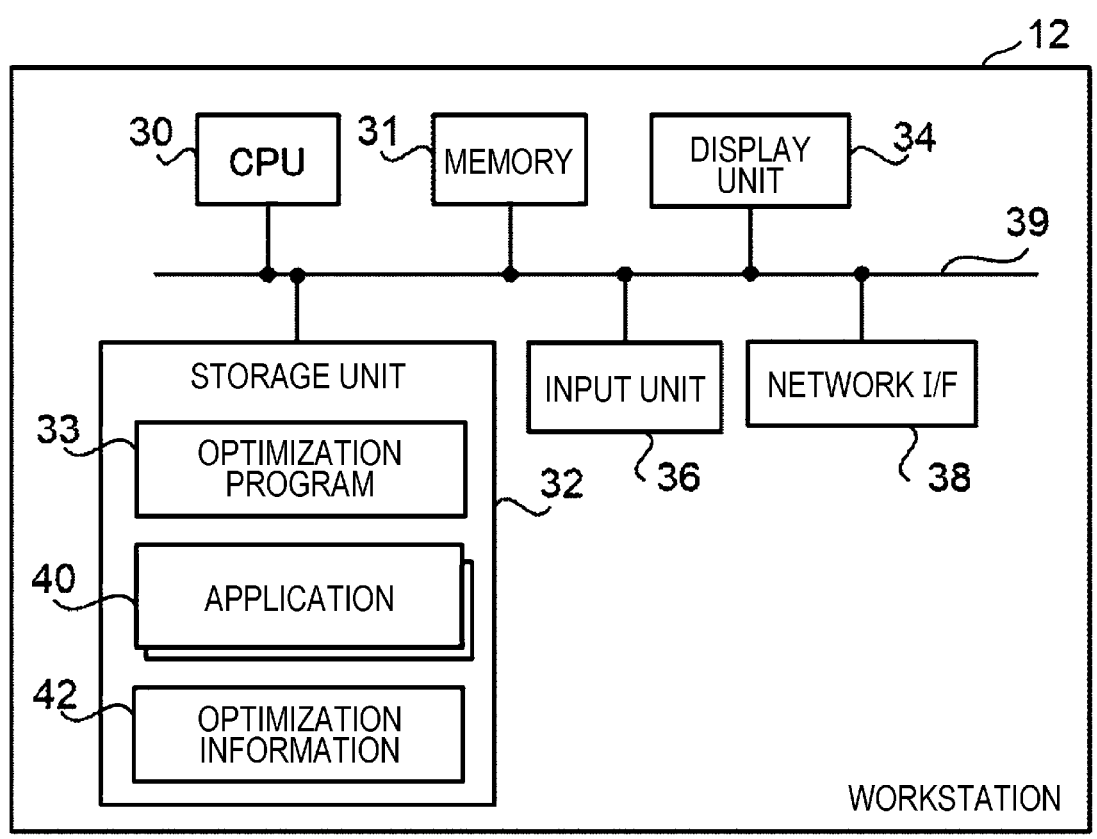
FIG. 3 is a block diagram illustrating an example hardware configuration of a workstation.

Next, an example hardware configuration of the workstation 12 of the present embodiment will be described with reference to FIG. 3. As illustrated in FIG. 3, the workstation 12 includes a CPU 30, a memory 31, which is a temporary memory area, and a storage unit 32, which is a nonvolatile memory. The CPU 20 and the CPU 30 of the present embodiment are examples of a processor in the present disclosure, and the storage unit 22 and the storage unit 32 of the present embodiment are examples of a memory in the present disclosure.

The workstation 12 includes a display unit 34, which is, for example, a liquid crystal display, an input unit 36, which is, for example, a keyboard or a mouse, and a network I/F 38, which is connected to the network N. Note that the display unit 34 and the input unit 36 may be integrated into a touch panel display. The CPU 30, the memory 31, the storage unit 32, the display unit 34, the input unit 36, and the network I/F 38 are connected to a bus 39 so as to be able to communicate with each other.

The storage unit 32 is implemented as, for example, an SSD or a flash memory. In the storage unit 32 that is a storage medium, an optimization program 33 is stored. The CPU 30 reads from the storage unit 32 and loads to the memory 31 the optimization program 33 and executes the loaded optimization program 33. The automatic image analysis processing program 23 and the optimization program 33 of the present embodiment are examples of the information processing program in the present disclosure.

In the storage unit 32, a plurality of types of application programs (hereinafter simply referred to as "applications") 40 are stored. In other words, in the storage unit 32, a plurality of applications 40 are stored. Each of the plurality of applications 40 is a program for performing the second process.

In the storage unit 32, optimization information 42 for optimizing the applications 40 to be executed, the priority ranks of the applications 40 to be executed, and a retention period for which the execution result of the applications 40 is to be retained is stored. The optimization information 42 is information indicating one or more processes to be performed as the second process, which are determined in advance and which are performed depending on the processing result of the first process, among processes performable by the plurality of applications 40. For example, in a case where a medical image for image analysis is a medical image conforming to the DICOM (Digital Imaging and Communications in Medicine) standard, the plurality of processes performable in the present embodiment are processes determined in advance in accordance with a DICOM tag. Examples of the DICOM tag include Image Comments and Study Description.

FIG. 4 illustrates an example of the optimization information 42. As illustrated in FIG. 4, the optimization information 42 is information indicating a correspondence between the first process that is performed by the automatic processing server 10 and the processing result of the first process, and one or more processes that are performed by the workstation 12 as the second process, the retention period of the processing result of the second process, and the priority ranks of the one or more processes that are performed as the second process.

Next, a functional configuration of the automatic processing server 10 and that of the workstation 12 of the present embodiment will be described with reference to FIG. 5. As illustrated in FIG. 5, the automatic processing server 10 includes an obtaining unit 50 and a first processing unit 52. The CPU 20 executes the automatic image analysis processing program 23 to thereby function as the obtaining unit 50 and the first processing unit 52.

The obtaining unit 50 obtains a medical image. More specifically, the obtaining unit 50 obtains image data representing a medical image. Note that the obtaining unit 50 may obtain a medical image from any source. For example, a medical image may be obtained from PACS (Picture Archiving and Communication System) where a desired medical image is retained. For example, a form may be employed in which a medical image directly input to the automatic processing server 10 by, for example, a user using the input unit 26 is obtained. The medical image obtained by the obtaining unit 50 is output to the first processing unit 52.

The first processing unit 52 performs the first process, which is image processing performed for the medical image input from the obtaining unit 50. Note that there is no limitation on the configuration of the first processing unit 52, and the first processing unit 52 may be, for example, a processing unit that uses artificial intelligence (AI).

The first processing unit 52 may perform a plurality of first processes. The first process performed by the first processing unit 52 may include a plurality of processes. For example, as the first process, the first processing unit 52 may perform a plurality of processes including bone fracture CAD (Computer Aided Diagnosis) for detecting the presence or absence of a bone fracture and tumor detection CAD for detecting the presence or absence of a tumor. Further, for example, the tumor detection CAD may include a plurality of processes, such as a process for detecting the presence or absence of a tumor and a process for determining whether the tumor is malignant or benign.

Note that in a case where the medical image is a medical image conforming to the DICOM standard, the first process can be a process corresponding to a DICOM tag. Data representing the processing result of the first processing and image data representing the medical image subjected to the first process are output to the workstation 12 from the first processing unit 52.

As illustrated in FIG. 5, the workstation 12 includes an obtaining unit 60, a specifying unit 62, a second processing unit 64, and a retention control unit 66. The CPU 30 executes the optimization program 33 to thereby function as the obtaining unit 60, the specifying unit 62, the second processing unit 64, and the retention control unit 66.

The obtaining unit 60 obtains and outputs to the specifying unit 62 the image data representing the medical image subjected to the first process and the data representing the processing result of the first processing output from the automatic processing server 10.

The specifying unit 62 specifies, with reference to the optimization information 42, one or more processes to be performed as the second process, which are determined in advance and which depend on the processing result of the first processing, from among processes performable by the plurality of applications 40 for the input medical image. In a case where the second process includes a plurality of processes, the specifying unit 62 specifies, with reference to the optimization information 42, the priority ranks of the plurality processes included in the second process. The image data representing the medical image input to the specifying unit 62, information indicating the one or more processes specified by the specifying unit 62 as the second process, and information indicating the priority ranks for performing are output to the second processing unit 64.

The specifying unit 62 specifies, with reference to the optimization information 42, a retention period for which the processing result of the second process is to be retained and which depends on the processing result of the first processing. Retention period information indicating the retention period of the processing result of the second process specified by the specifying unit 62 is output to the retention control unit 66.

The second processing unit 64 performs the one or more processes included in the second process for the medical image input from the specifying unit 62 in accordance with the priority ranks specified by the specifying unit 62. Specifically, the second processing unit 64 performs the one or more processes specified by the specifying unit 62 as the second process for the image data representing the medical image subjected to the first process, in accordance with the priority ranks specified by the specifying unit 62. Note that there is no limitation on the configuration of the second processing unit 64, and the second processing unit 64 may be, for example, a processing unit that uses artificial intelligence. Data representing the processing result of the second process, which is, for example, image data representing the medical image subjected to the second process, is output to the retention control unit 66.

The retention control unit 66 performs control to retain the data representing the processing result of the second process input from the second processing unit 64 in the storage unit 22 for the retention period indicated by the retention period information input from the specifying unit 62. Note that the processing result of the second process need not be retained in the storage unit 22 and may be retained in an apparatus, such as PACS, other than the information processing system 1.

Figure 6:
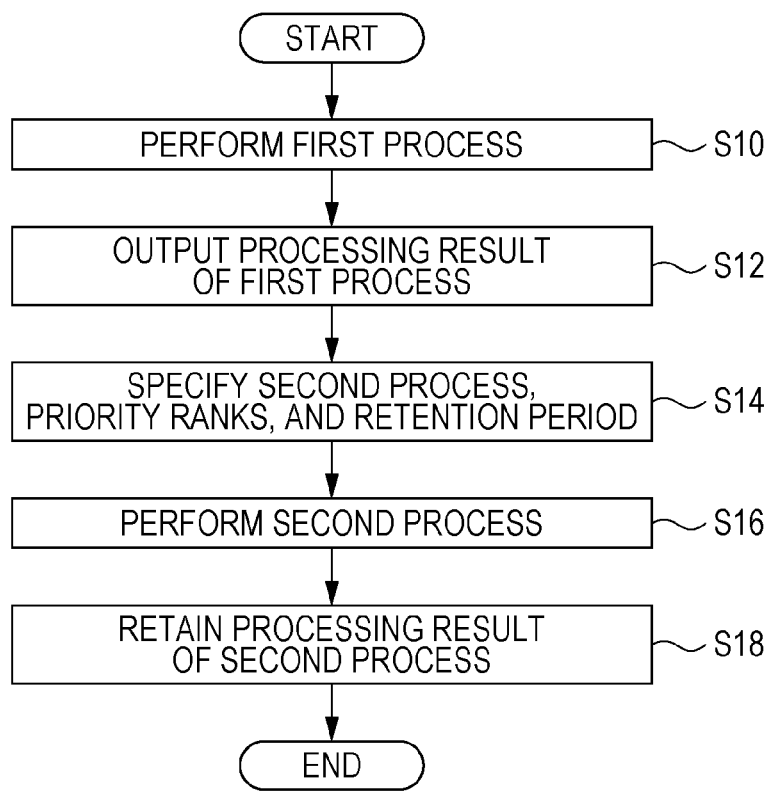
FIG. 6 is a flowchart illustrating an example flow of a series of processes performed for a medical image in the information processing system.

Next, operations of the information processing system 1 of the present embodiment will be described. The overall operations of the information processing system 1 will be described first with reference to FIG. 6. FIG. 6 illustrates an example flow of a series of processes performed in the information processing system 1 for a medical image. Among the series of processes illustrated in FIG. 6, the processes in steps S10 and S12 are performed by the automatic processing server 10, and the processes in steps S14, S16, and S18 are performed by the workstation 12.

In step S10 in FIG. 6, the first processing unit 52 of the automatic processing server 10 performs the first process for a medical image obtained by the obtaining unit 50 as described above. Next, in step S12, the first processing unit 52 of the automatic processing server 10 outputs information indicating the processing result of the first process to the workstation 12 together with image data representing the medical image subjected to the first process as described above.

Next, in step S14, the specifying unit 62 of the workstation 12 specifies, with reference to the optimization information 42, one or more processes that are to be performed for the medical image as the second process and that depend on the processing result of the first process, from among a plurality of processes performable by the plurality of applications 40 as described above. The specifying unit 62 specifies, with reference to the optimization information 42, priority ranks based on which the one or more processes that depend on the processing result of the first process are to be performed as the second process as described above. Further, the specifying unit 62 specifies, with reference to the optimization information 42, the retention period of the processing result of the second process, which depends on the processing result of the first process as described above.

Next, in step S16, the second processing unit 64 of the workstation 12 performs, as described above, the one or more processes specified in step S14 described above for the medical image subjected to the first process, as the second process in accordance with the priority ranks specified in step S14 described above.

Next, in step S18, the retention control unit 66 of the workstation 12 performs, as described above, control to retain the processing result of the second process performed in step S16 described above for the retention period specified in step S14 described above. When the process in step S18 ends, the series of processes for the medical image performed in the information processing system 1 ends.

Next, operations of the automatic processing server 10 and those of the workstation 12 among the operations of the information processing system 1 described above will be described in detail. In the present embodiment, operations of the automatic processing server 10 and those of the workstation 12 will be described in detail with two examples.

First Example

In a first example, an example case where the first process is bone fracture CAD (see the optimization information 42 in FIG. 4) for detecting a bone fracture as a matter of concern will be described. An example form in which the optimization information 42 illustrated in FIG. 4 described above is used as the optimization information 42 will be described.

Figure 7:
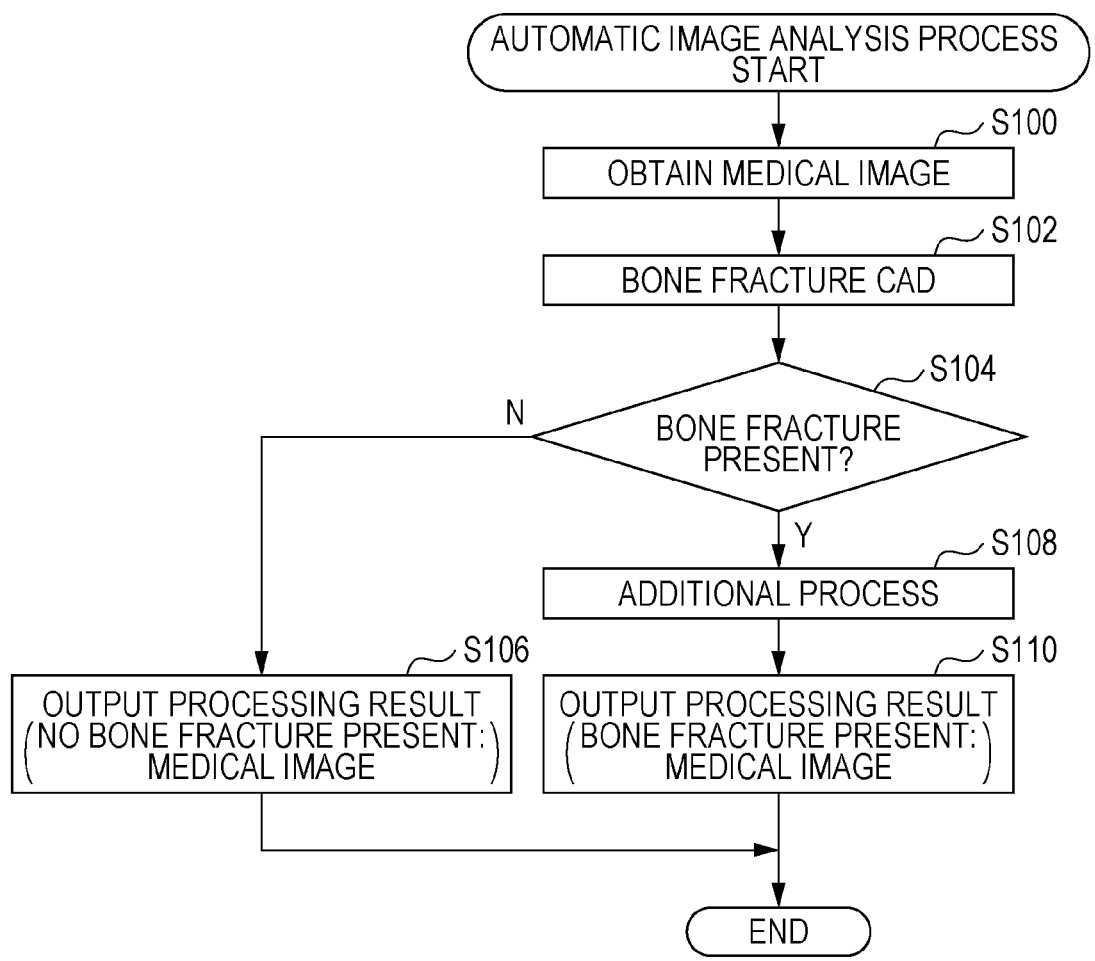
FIG. 7 is a flowchart illustrating an example of an automatic image analysis process performed by the automatic processing server in a first example.

Operations of the automatic processing server 10 in the first example will be described first with reference to FIG. 7. An automatic image analysis process illustrated in FIG. 7 is performed by the CPU 20 of the automatic processing server 10 executing the automatic image analysis processing program 23. The automatic image analysis process illustrated in FIG. 7 is a process for performing the processes in steps S10 and S12 in the series of processes described above (see FIG. 6). The automatic image analysis process illustrated in FIG. 7 is performed, for example, periodically at predetermined time intervals.

In step S100 in FIG. 7, the obtaining unit 50 obtains image data representing a medical image as described above. Next, in step S102, the first processing unit 52 performs bone fracture CAD, which is the first process, for the medical image and detects the presence or absence of a bone fracture in a bone included in the medical image. For example, in a case where the medical image is, for example, a radiological image or a CT (Computed Tomography) image of the chest of a subject, the first processing unit 52 detects the presence or absence of a bone fracture in a rib by bone fracture CAD.

Next, in step S104, the first processing unit 52 determines whether a bone fracture is present. If a detection result indicating that no bone fracture is present is obtained, determination in step S104 results in negative determination, and the flow proceeds to step S106.

In step S106, the first processing unit 52 outputs, as described above, the processing result obtained in step S102 described above. Specifically, the first processing unit 52 outputs to the workstation 12 information indicating that no bone fracture is present and image data representing the medical image subjected to bone fracture CAD performed in step S102 described above, as the processing result of the first process. When the process in step S106 ends, the automatic image analysis process ends.

On the other hand, if a detection result indicating that a bone fracture is present is obtained in step S102 described above, determination in step S104 described above results in positive determination, and the flow proceeds to step S108. In step S108, the first processing unit 52 performs an additional process for the medical image subjected to bone fracture CAD performed in step S102 described above. The additional process is a process included in the first process. Examples of the additional process in the first process in the first example include a process of classification according to the type of bone fracture, labeling for showing the type of bone, and segmentation.

Next, in step S110, the first processing unit 52 outputs, as described above, the processing results obtained in steps S102 and S108 described above. Specifically, the first processing unit 52 outputs to the workstation 12 information indicating that a bone fracture is present and image data representing the medical image subjected to the additional process performed in step S108 described above, as the processing result of the first process. When the process in step S110 ends, the automatic image analysis process ends.

Figure 8:
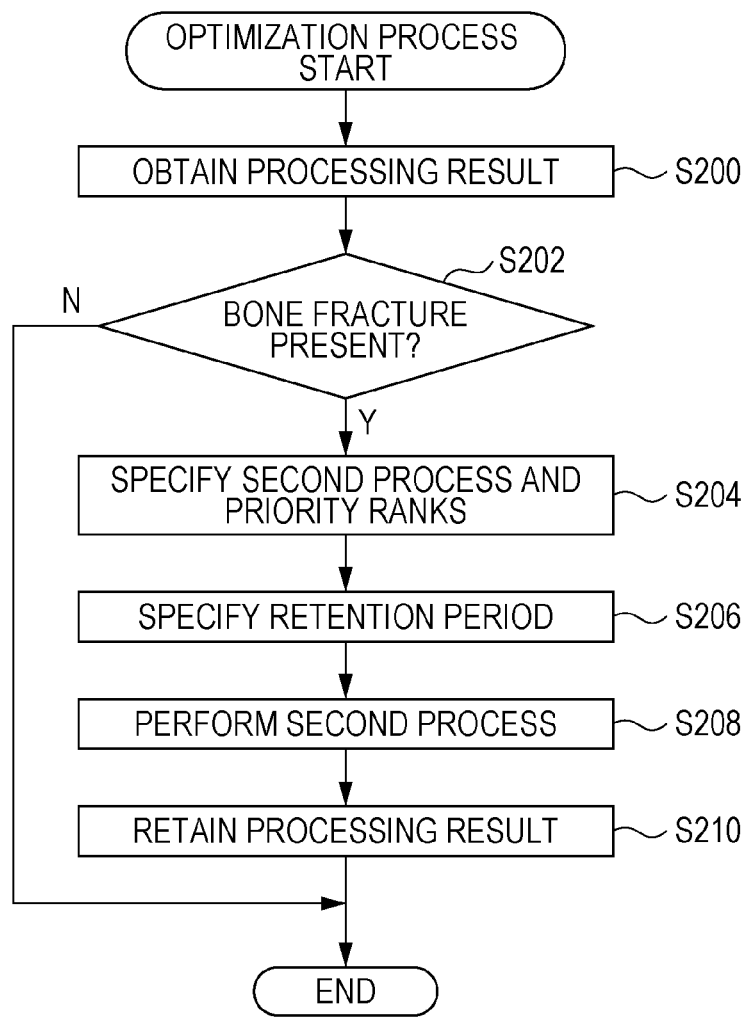
FIG. 8 is a flowchart illustrating an example of an optimization process performed by the workstation in the first example.

Next, operations of the workstation 12 in the first example will be described with reference to FIG. 8. An optimization process illustrated in FIG. 8 is performed by the CPU 30 of the workstation 12 executing the optimization program 33. The optimization process illustrated in FIG. 8 is a process for performing the processes in steps S14 to S18 in the series of processes described above (see FIG. 6). The optimization process illustrated in FIG. 8 is, for example, performed at the timing when the processing result of the first process is input from the automatic processing server 10 or performed periodically at predetermined intervals.

In step S200 in FIG. 8, the obtaining unit 60 obtains data representing the processing result of the first process and image data representing a medical image subjected to the first process as described above. Next, in step S202, the specifying unit 62 determines whether the processing result obtained in step S200 described above is a detection result indicating that a bone fracture is present. If the processing result of the first process is not a detection result indicating that a bone fracture is present, that is, is a detection result indicating that no bone fracture is present, determination in step S202 results in negative determination. As indicated by the optimization information 42, no second process is associated with the first process "bone fracture CAD" and the processing result "no bone fracture is present". Specifically, the optimization information 42 does not include information regarding the processing result "no bone fracture is present" for the first process "bone fracture CAD". Therefore, if determination in step S202 results in negative determination, the optimization process ends. As described above, the workstation 12 in the first example performs no second process if the processing result of the first process is a detection result indicating that no bone fracture is present. Note that even in such a case where no second process is performed, it is preferable to store the image data obtained from the automatic processing server 10 and representing the medical image subjected to the first process in a predetermined storage unit, such as the storage unit 32. Even in a case where no second process is performed in the optimization process, the second processing unit 64 of the workstation 12 needs to perform the second process in response to a user instruction being accepted later.

On the other hand, if the processing result of the first process is a detection result indicating that a bone fracture is present, determination in step S202 results in positive determination, and the flow proceeds to step S204. In step S204, the specifying unit 62 specifies, with reference to the optimization information 42, one or more processes to be performed as the second process and the priority ranks of the one or more processes to be performed as described above. In the optimization information 42 illustrated in FIG. 4, as the second process, processes including "three-dimensional image generation" having the first priority rank and "surface display" having the second priority rank are associated with the first process "bone fracture CAD" and the processing result "a bone fracture is present". The "three-dimensional image generation" process is a process of generating a three-dimensional image of the bone. The "surface display" process is a process of generating a polygon model for displaying the bone.

Next, in step S206, the specifying unit 62 specifies the retention period of the processing result of the second process with reference to the optimization information 42 as described above. In the first example, the specifying unit 62 specifies "six months" as the retention period from the optimization information 42 illustrated in FIG. 4.

Next, in step S208, the second processing unit 64 performs, as described above, the one or more processes as the second process on the basis of the specification result obtained in step S204 described above. In the first example, the second processing unit 64 first selects the application 40 for performing the "three-dimensional image generation" process and executes the selected application 40 for the medical image. Next, the second processing unit 64 selects the application 40 for performing the "surface display" process and executes the selected application 40 for the medical image.

When the second process by the second processing unit 64 is completed accordingly, next, in step S210, the retention control unit 66 performs, as described above, control to retain the processing result of the second process performed in step S208 described above on the basis of the specification result obtained in step S206 described above. In the first example, the retention control unit 66 performs control to retain the processing result of the second process for "six months". When the process in step S210 ends, the optimization process ends.

Second Example

In a second example, an example case where the first process is tumor detection CAD (see the optimization information 42 in FIG. 4) for detecting a tumor as a matter of concern will be described. An example form in which the optimization information 42 illustrated in FIG. 4 described above is used as the optimization information 42 will be described.

Figure 9:
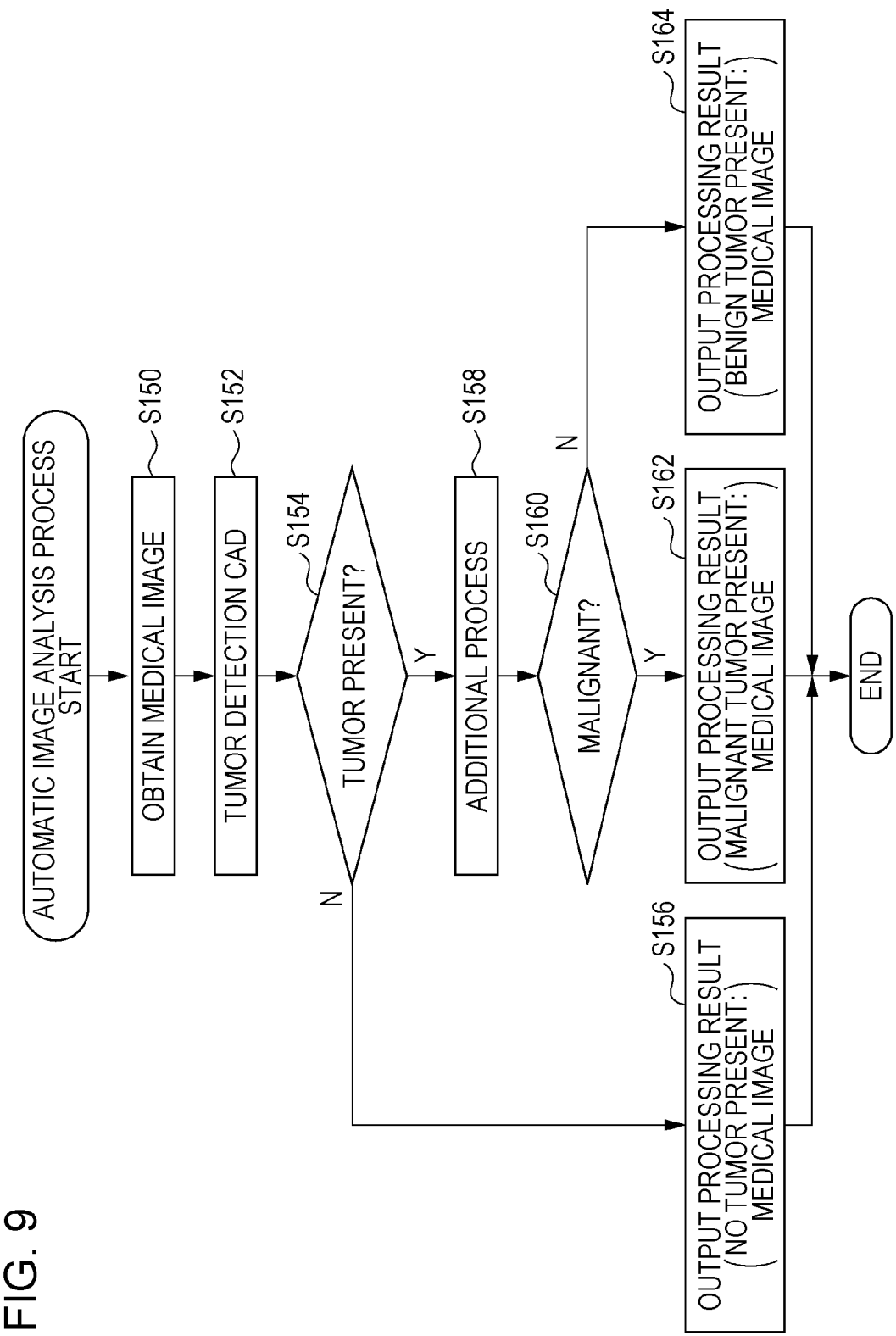
FIG. 9 is a flowchart illustrating an example of the automatic image analysis process performed by the automatic processing server in a second example.

Operations of the automatic processing server 10 in the second example will be described first with reference to FIG. 9. An automatic image analysis process illustrated in FIG. 9 is performed by the CPU 20 of the automatic processing server 10 executing the automatic image analysis processing program 23 as in the first example. The automatic image analysis process illustrated in FIG. 9 is a process for performing the processes in steps S10 and S12 in the series of processes described above (see FIG. 6). The automatic image analysis process illustrated in FIG. 9 is performed, for example, periodically at predetermined time intervals.

In step S150 in FIG. 9, the obtaining unit 50 obtains image data representing a medical image as in step S100 in the automatic image analysis process in the first example described above (see FIG. 7). Next, in step S152, the first processing unit 52 performs tumor detection CAD, which is the first process, for the medical image and detects the presence or absence of a tumor included in the medical image. For example, in a case where the medical image is, for example, a radiological image or a CT image of the lung (chest) of a subject, the first processing unit 52 detects the presence or absence of a tumor in the lung by tumor detection CAD.

Next, in step S154, the first processing unit 52 determines whether a tumor is present. If a detection result indicating that no tumor is present is obtained, determination in step S154 results in negative determination, and the flow proceeds to step S156.

In step S156, the first processing unit 52 outputs, as described above, the processing result obtained in step S152 described above. Specifically, the first processing unit 52 outputs to the workstation 12 information indicating that no tumor is present and image data representing the medical image subjected to tumor detection CAD performed in step S152 described above, as the processing result of the first process. When the process in step S156 ends, the automatic image analysis process ends.

On the other hand, if a detection result indicating that a tumor is present is obtained in step S152 described above, determination in step S154 described above results in positive determination, and the flow proceeds to step S158. In step S158, the first processing unit 52 performs an additional process for the medical image subjected to tumor detection CAD performed in step S152 described above. The additional process is a process included in the first process. Examples of the additional process in the first process in the second example include a process for determining whether the tumor is benign or malignant and segmentation of the tumor or other organs.

Next, in step S160, the first processing unit 52 determines whether the tumor is malignant. If it is determined as a result of the additional process performed in step S158 described above that the tumor is malignant, determination in step S160 results in positive determination, and the flow proceeds to step S162. In step S162, the first processing unit 52 outputs, as described above, the processing results obtained in steps S152 and S158 described above. Specifically, the first processing unit 52 outputs to the workstation 12 information indicating that a tumor is present as the processing result of the first process, information indicating that the tumor is malignant as the processing result of the additional process, and image data representing the medical image subjected to the additional process. When the process in step S162 ends, the automatic image analysis process ends.

On the other hand, if it is determined that the tumor is benign, determination in step S160 results in negative determination, and the flow proceeds to step S164. In step S164, the first processing unit 52 outputs, as described above, the processing results obtained in steps S152 and S158 described above. Specifically, the first processing unit 52 outputs to the workstation 12 information indicating that a tumor is present as the processing result of the first process, information indicating that the tumor is benign as the processing result of the additional process, and image data representing the medical image subjected to the additional process. When the process in step S164 ends, the automatic image analysis process ends.

Figure 10:
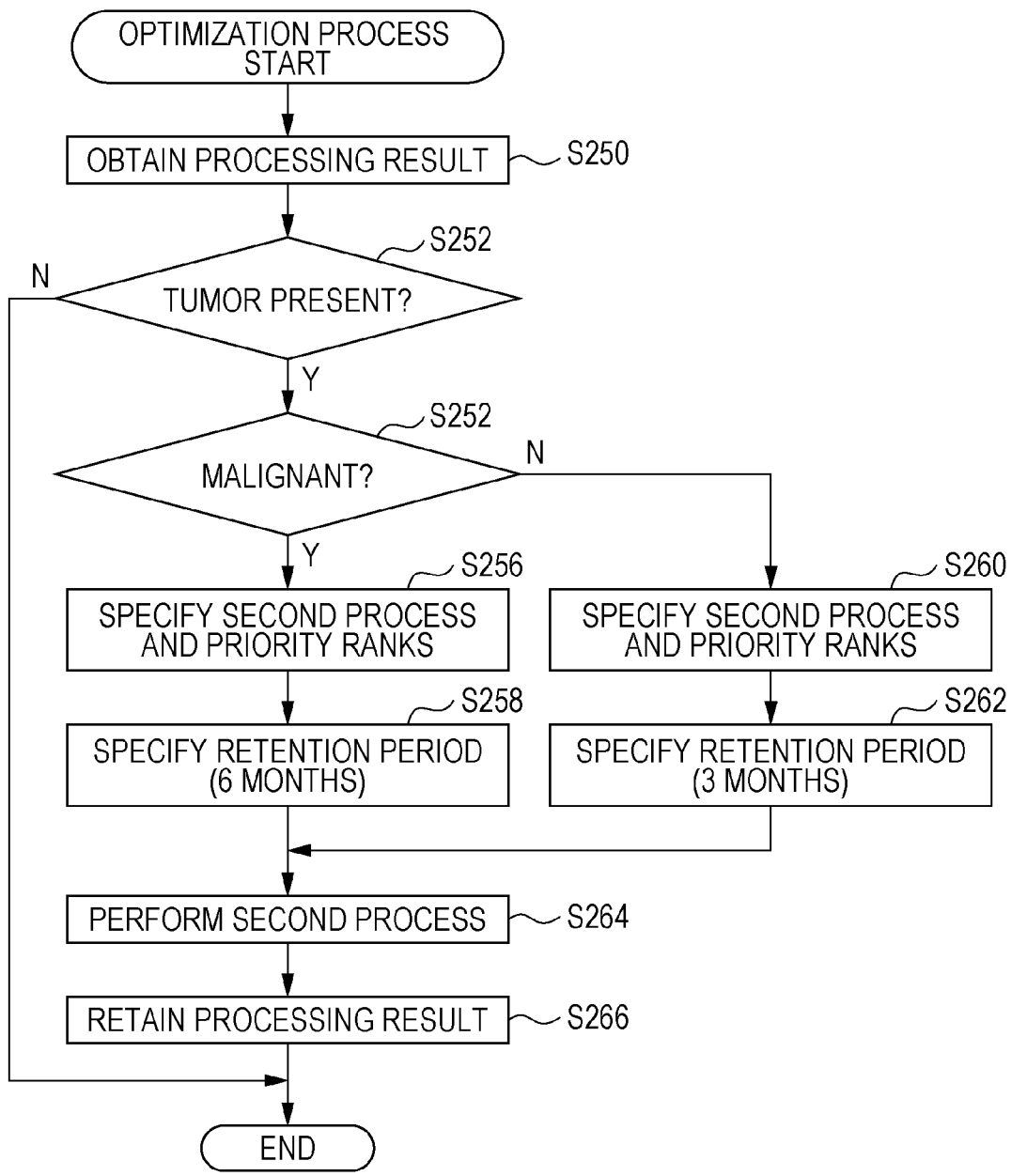
FIG. 10 is a flowchart illustrating an example of the optimization process performed by the workstation in the second example.

Next, operations of the workstation 12 in the second example will be described with reference to FIG. 10. An optimization process illustrated in FIG. 10 is performed by the CPU 30 of the workstation 12 executing the optimization program 33 as in the first example. The optimization process illustrated in FIG. 10 is a process for performing the processes in steps S14 to S18 in the series of processes described above (see FIG. 6). The optimization process illustrated in FIG. 10 is, for example, performed at the timing when the processing result of the first process is input from the automatic processing server 10 or performed periodically at predetermined intervals.

In step S250 in FIG. 10, the obtaining unit 60 obtains data representing the processing result of the first process and image data representing a medical image subjected to the first process as in step S200 in the optimization process in the first example described above (see FIG. 8). Next, in step S252, the specifying unit 62 determines whether the processing result obtained in step S250 described above includes a result indicating that a tumor is present. If the processing result of the first process does not include a result indicating that a tumor is present, that is, includes a processing result indicating that no tumor is present, determination in step S252 results in negative determination.

As indicated by the optimization information 42, no second process is associated with the first process "tumor detection CAD" and the processing result "no tumor is present". Specifically, the optimization information 42 does not include information regarding the processing result "no tumor is present" for the first process "tumor detection CAD". Therefore, if determination in step S252 results in negative determination, the optimization process ends. As described above, the workstation 12 in the second example performs no second process if the processing result of the first process includes a result indicating that no tumor is present. Note that even in such a case where no second process is performed, it is preferable to store the image data obtained from the automatic processing server 10 and representing the medical image subjected to the first process in a predetermined storage unit, such as the storage unit 32, as in the first example. Even in a case where no second process is performed in the optimization process, the second processing unit 64 of the workstation 12 needs to perform the second process in response to a user instruction being accepted later.

On the other hand, if the processing result of the first process includes a result indicating that a tumor is present, determination in step S252 results in positive determination, and the flow proceeds to step S254. In step S254, the specifying unit 62 determines whether the tumor is malignant. If the processing result of the first process includes a result indicating that the tumor is malignant, determination in step S254 results in positive determination, and the flow proceeds to step S256.

In step S256, the specifying unit 62 specifies, with reference to the optimization information 42, one or more processes to be performed as the second process and the priority ranks of the one or more processes to be performed as described above. In the optimization information 42 illustrated in FIG. 4, as the second process, processes including "metastasis analysis" having the first priority rank, "past image comparison" having the second priority rank, and "three-dimensional image generation" having the third priority rank are associated with the first process "tumor detection CAD" and the processing result "a tumor is present" and "malignant". The "metastasis analysis" is an analysis process performed for an organ to which the tumor is suspected to metastasize, on the basis of, for example, the result of segmentation. The "past image comparison" is a process of comparing the medical image captured this time with a medical image of the same subject captured in the past. For example, in a case of a malignant tumor that is suspected to metastasize to a bone, when the difference between medical images captured at different times is obtained, a change can be easily recognized. The "three-dimensional image generation" process is a process of generating a three-dimensional image of the lung.

Next, in step S258, the specifying unit 62 specifies the retention period of the processing result of the second process with reference to the optimization information 42 as described above. In the second example, the specifying unit 62 specifies "six months" as the retention period from the optimization information 42 illustrated in FIG. 4.

On the other hand, if the processing result of the first process includes a result indicating that the tumor is benign, determination in step S254 results in negative determination, and the flow proceeds to step S260. In step S260, the specifying unit 62 specifies, with reference to the optimization information 42, one or more processes to be performed as the second process and the priority ranks of the one or more processes to be performed as described above. In the optimization information 42 illustrated in FIG. 4, as the second process, processes including "metastasis analysis" having the first priority rank and "three-dimensional image generation" having the second priority rank are associated with the first process "tumor detection CAD" and the processing result "a tumor is present" and "benign". As described above, in a case of a benign tumor that is less likely to metastasize, unlike in a case of a malignant tumor, "past image comparison" is not associated as the second process.

Next, in step S262, the specifying unit 62 specifies the retention period of the processing result of the second process with reference to the optimization information 42 as described above. In the second example, the specifying unit 62 specifies "three months" as the retention period from the optimization information 42 illustrated in FIG. 4.

In step S264 subsequent to step S258 or S262, the second processing unit 64 performs, as described above, the one or more processes as the second process on the basis of the specification result obtained in step S256 or S260 described above. In the second example, in a case where step S264 is performed after step S258, the second processing unit 64 first selects the application 40 for performing the "metastasis analysis" process and executes the selected application 40 for the medical image. Next, the second processing unit 64 selects the application 40 for performing the "past image comparison" process and executes the selected application 40 for the medical image. Further, the second processing unit 64 selects the application 40 for performing the "three-dimensional image generation" process and executes the selected application 40 for the medical image. On the other hand, in a case where step S264 is performed after step S262, the second processing unit 64 first selects the application 40 for performing the "metastasis analysis" process and executes the selected application 40 for the medical image. Next, the second processing unit 64 selects the application 40 for performing the "three-dimensional image generation" process and executes the selected application 40 for the medical image.

When the second process by the second processing unit 64 is completed accordingly, next, in step S266, the retention control unit 66 performs, as described above, control to retain the processing result of the second process in step S264 on the basis of the specification result obtained in step S258 or S262 described above. In the second example, in a case where the process in step S258 is performed, the retention control unit 66 performs control to retain the processing result of the second process in step S264 for "six months". On the other hand, in a case where the process in step S262 is performed, the retention control unit 66 performs control to retain the processing result of the second process in step S264 for "three months". When the process in step S266 ends, the optimization process ends.

As described above, the information processing system 1 of the present embodiment includes the automatic processing server 10 that includes the CPU 20 and the storage unit 22 storing instructions executable by the CPU 20, and the workstation 12 that includes the CPU 30 and the storage unit 32 storing instructions executable by the CPU 30. The CPU 20 carries out an image analysis for a medical image as the first process. The CPU 30 specifies one or more processes to be performed as the second process, which are determined in advance and which depend on the processing result of the first process, from among a plurality of processes performable by the plurality of applications 40 and performs the one or more processes as the second process for the medical image subjected to the first process.

Unlike in the information processing system 1 of the present embodiment, in a case where one or more processes that do not depend on the processing result of the first process and that are determined in advance in accordance with information attached to a medical image are performed as the second process, a process having a relatively low degree of necessity for the user may be performed. For example, even in a case where a matter of concern, such as a bone fracture or a tumor, is not detected from a medical image, a process necessary for observing and diagnosing a bone fracture or a tumor may be performed as the second process. In such a case, for example, the load of the memory of the workstation 12 that performs the second process increases, and the processing load increases. To retain the processing result of the second process, the amount of use of, for example, the storage unit 32 increases.

In contrast, in the information processing system 1 of the present embodiment, in a case where a plurality of processes are performable for a medical image, one or more processes to be performed for the medical image as the second process are specified from among the plurality of processes in accordance with the processing result of the first process as described above. Therefore, with the information processing system 1 of the present embodiment, it is possible to optimize the second process that is performed for a medical image after the first process and to prevent a process having a relatively low degree of necessity for the user from being performed. Accordingly, with the information processing system 1 of the present embodiment, it is possible to suppress an increase in the processing load of the workstation 12 that performs the second process. Further, it is possible to suppress an increase in the amount of use of, for example, the storage unit 32 that retains the processing result of the second process.

Although a case where the medical image is a medical image conforming to the DICOM standard has been described in the present embodiment, the form of the medical image is not limited to a form conforming to the DICOM standard. For example, the form may be a form conforming to other standards including the HL7-CDA (Clinical Document Architecture) standard and the "ASTM-CCR (American Society for Testing and Materials-Continuity of Care Record)" standard.

Although a form in which the optimization information 42 of the present embodiment is information indicating one or more processes to be performed as the second process, which are determined in advance and which are performed depending on the processing result of the first process, among processes performable by the plurality of applications 40 has been described, the optimization information 42 is not limited to this form. For example, a form may be employed in which the optimization information 42 is information indicating one or more processes that are determined not to be performed as the second process depending on the processing result of the first process, among processes performable by the plurality of applications 40. In this case, the specifying unit 62 of the workstation 12 specifies one or more processes that are not to be performed as the second process.

As the hardware configuration of processing units that perform various types of processing by, for example, the functional units of the automatic processing server 10 and the workstation 12 according to the present embodiment, various processors described below can be used. The various processors include a CPU, which is a general-purpose processor executing software (program) as described above to function as various processing units, a programmable logic device (PLD), such as an FPGA (field-programmable gate array), which is a processor having a circuit configuration that is changeable after manufacture, and a dedicated electric circuit, such as an ASIC (application-specific integrated circuit), which is a processor having a circuit configuration specifically designed to perform specific processing.

One processing unit may be configured as one of the various processors or two or more processors of the same type or different types (for example, a combination of a plurality of FPGAs or a combination of a CPU and an FPGA). Further, a plurality of processing units may be configured as one processor.

As the first example of configuring a plurality of processing units as one processor, a form is possible where one or more CPUs and software are combined to configure one processor, and the processor functions as the plurality of processing units, representative examples of which are computers, such as a client and a server. As the second example thereof, a form is possible where a processor is used in which the functions of the entire system including the plurality of processing units are implemented as one IC (integrated circuit) chip, a representative example of which is a system on chip (SoC). As described above, regarding the hardware configuration, the various processing units are configured by using one or more of the various processors described above.

Further, as the hardware configuration of the various processors, more specifically, an electric circuit (circuitry) in which circuit elements, such as semiconductor elements, are combined can be used.

Although a form in which the automatic image analysis processing program 23 is stored (installed) in advance in the storage unit 22 and the optimization program 33 is stored in advance in the storage unit 32 has been described in the present embodiment, the automatic image analysis processing program 23 and the optimization program 33 are not limited to this. Each of the automatic image analysis processing program 23 and the optimization program 33 may be recorded to a recording medium, such as a CD-ROM (compact disc read-only memory), a DVD-ROM (digital versatile disc read-only memory), or a USB (universal serial bus) memory, and provided. A form may be employed in which each of the automatic image analysis processing program 23 and the optimization program 33 is downloaded from an external apparatus over a network.

REFERENCE SIGNS LIST 1 information processing system
10 automatic processing server
12 workstation
20, 30 CPU
21, 31 memory
22, 32 storage unit
23 automatic image analysis processing program
24, 34 display unit
26, 36 input unit
28, 38 network OF
29, 39 bus
33 optimization program
40 application
42 optimization information
50, 60 obtaining unit
52 first processing unit
62 specifying unit
64 second processing unit
66 retention control unit
N network

What is claimed is:

1. An information processing system comprising:
at least one processor; and
a memory configured to store an instruction and optimization information of a plurality of processes, executable by the processor,
the processor being configured to
carry out an image analysis for a medical image as a first process,
specify, referring to the optimization information, a second process that depends on a processing result of the first process, from among the plurality of processes,
specify, in a case where the second process includes two or more processes, priority ranks of the two or more processes depending on the processing result of the first process, and
perform the two or more processes included in the second process on the basis of the specified priority ranks for the medical image subjected to the first process,
wherein the optimization information includes information indicating a correspondence between the processing result of the first process and at least one of the plurality of processes that are performed depending on the processing results of the first process, a retention period of the processing results of the plurality of processes or priority ranks of performing the plurality of processes.

2. The information processing system according to claim 1, wherein
the processor is configured to
specify a retention period of a processing result of the second process, the retention period depending on the processing result of the first process, and
retain the processing result of the second process for the specified retention period.

3. The information processing system according to claim 1, wherein
the processor is configured to
specify a process that is not to be performed as the second process from among the plurality of processes.

4. The information processing system according to claim 1, wherein
the first process includes a process of detecting presence or absence of a matter of concern from the medical image, and
the processor is configured to not specify the second process in a case where the processing result of the first process includes a detection result indicating that the matter of concern is not present.

5. The information processing system according to claim 1, wherein
the medical image is a medical image conforming to a DICOM (Digital Imaging and Communications in Medicine) standard, and
the plurality of processes are processes determined in accordance with a tag of the DICOM.

6. An information processing system comprising:
a first processing apparatus comprising at least one processor; and a second processing apparatus comprising at least one processor and a storage that stores optimization information of a plurality of processes executable by the processor,
the processor of the first processing apparatus being configured to
carry out an image analysis for a medical image as a first process,
the processor of the second processing apparatus being configured to
specify, referring to the optimization information, a second process that depends on a processing result of the first process, from among the plurality of processes,
specify, in a case where the second process includes two or more processes, priority ranks of the two or more processes depending on the processing result of the first process, and
perform the two or more processes included in the second process on the basis of the specified priority ranks for the medical image subjected to the first process,
wherein the optimization information includes information indicating a correspondence between the processing result of the first process and at least one of the plurality of processes that are performed depending on the processing results of the first process, a retention period of the processing results of the plurality of processes or priority ranks of performing the plurality of processes.

7. An information processing method in which a computer performs a process comprising:
carrying out an image analysis for a medical image as a first process,
specifying, referring to optimization information of a plurality of processes, a second process that depends on a processing result of the first process, from among a plurality of processes,
specifying, in a case where the second process includes two or more processes, priority ranks of the two or more processes depending on the processing result of the first process, and
performing the two or more processes included in the second process on the basis of the specified priority ranks for the medical image subjected to the first process,
wherein the optimization information includes information indicating a correspondence between the processing result of the first process and at least one of the plurality of processes that are performed depending on the processing results of the first process, a retention period of the processing results of the plurality of processes or priority ranks of performing the plurality of processes.

8. A non-transitory computer readable recording medium storing an information processing program for causing a computer to perform a process comprising:
carrying out an image analysis for a medical image as a first process,
specifying, referring to the optimization information of a plurality of processes, a second process that depends on a processing result of the first process, from among a plurality of processes,
specifying, in a case where the second process includes two or more processes, priority ranks of the two or more processes depending on the processing result of the first process, and
performing the two or more processes included in the second process on the basis of the specified priority ranks for the medical image subjected to the first process,
wherein the optimization information includes information indicating a correspondence between the processing result of the first process and at least one of the plurality of processes that are performed depending on the processing results of the first process, a retention period of the processing results of the plurality of processes or priority ranks of performing the plurality of processes.

9. An information processing system comprising:
at least one processor; and
a memory configured to store an instruction and optimization information of a plurality of processes, executable by the processor,
the processor being configured to
carry out an image analysis for a medical image as a first process,
specify, referring to the optimization information, a second process in accordance with a processing result of the first process and priority ranks of performing the plurality of processes, from among the plurality of processes, and
perform the optimized second process for the medical image subjected to the first process,
wherein the optimization information includes information indicating a correspondence between the processing result of the first process and at least one of the plurality of processes, and each of the plurality of processes corresponds to a priority rank of performing the plurality of processes.

* * * * *